United States Patent [19]
Grim

[11] Patent Number: 5,554,104
[45] Date of Patent: Sep. 10, 1996

[54] CUSTOM FORMABLE KNEE BRACE

[75] Inventor: Tracy E. Grim, Broken Arrow, Okla.

[73] Assignee: Royce Medical Company, Camarillo, Calif.

[21] Appl. No.: 349,021

[22] Filed: Dec. 2, 1994

Related U.S. Application Data

[63] Continuation-in-part of Ser. No. 993,121, Dec. 18, 1992, abandoned.

[51] Int. Cl.$^6$ ..................................................... A61F 5/00
[52] U.S. Cl. ..................... 602/8; 602/6; 602/16; 602/23; 602/26
[58] Field of Search ................................. 602/5, 16, 23, 602/26, 6, 8

[56] References Cited

U.S. PATENT DOCUMENTS

| | | |
|---|---|---|
| 4,852,557 | 8/1989 | Grim . |
| 4,928,678 | 5/1990 | Grim . |
| 4,953,543 | 9/1990 | Grim et al. . |
| 4,986,264 | 1/1991 | Miller . |
| 4,996,979 | 3/1991 | Grim et al. . |
| 5,042,464 | 8/1991 | Skwor et al. . |
| 5,060,640 | 10/1991 | Rasmusson . |

*Primary Examiner*—Linda C. Dvorak
*Attorney, Agent, or Firm*—Poms, Smith, Lande & Rose, Professional Corporation

[57] ABSTRACT

A soft-goods type, custom "in situ" formable knee brace for supporting weakened or injured knees is disclosed having formable components which conform to the unique configuration of an individual's leg surfaces. A flexible femoral component, extending circumferentially around the anterior femur, is pivotally connected with a flexible tibial component extending circumferentially around the anterior tibia. The pivoting hinge assemblies have their axes of rotation oriented along the axis of rotation of the knee joint, and may include condylar component pads. The initially flexible femoral and tibial components are secured to the leg and held in place by adjustable straps, and may be removed or adjusted by releasing or tightening the straps. The knee brace conforms to the leg surfaces through the use of a gas and liquid permeable matrix impregnated with a water-activated urethane polymer comprising, or contained within, each component. After tightening the knee brace around the upper and lower leg, and positioning the condylar component pads on opposite sides of the knee joint, the application of water to the matrix activates the urethane polymer which causes the components to harden into a substantially rigid structural member conforming to the unique shape of the individual's leg surfaces. An inlet duct may be included to introduce water into the matrix, and an outlet vent may be provided to permit the escape of air and gases. Padding is provided on each component for comfort. A calf component may be included to provide additional customized support.

20 Claims, 3 Drawing Sheets

CUSTOM FORMABLE KNEE BRACE

CROSS-REFERENCE TO RELATED APPLICATIONS

This is a continuation-in-part of commonly-owned, U.S. patent application Ser. No. 07/993,121, filed Dec. 18, 1992, now abandoned.

BACKGROUND OF THE INVENTION

1. Field of the Invention

The present invention relates generally to knee braces for injured or weakened knees, and, more particularly, to functional knee braces of the type suitable for athletes having weakened or torn knee ligaments, or other substantial knee injury.

2. Background of the Invention

In the orthopaedic knee brace or support field, relatively simple knee braces may be used for normal postoperative recovery, or for minor knee problems or injuries.

However, for major knee injuries, and/or when the user wishes to engage in vigorous athletic activities, a carefully molded functional knee brace is often prepared. The process for making these functional knee braces is moderately complicated, and involves initially making a mold of the users leg, and subsequently casting fiber reinforced resin to form the femoral (upper leg) and tibial (lower leg) components which are joined by struts and suitable hinge or pivot arrangements of known configurations. These preparation steps are time-consuming, complicated, and expensive.

Many techniques and systems have been proposed to reduce the weight and bulk of the knee brace, while insuring a snug fit. While many patented orthopaedic knee braces have claimed these improvements, in fact, none has disclosed a custom "in situ" formable knee brace having a low-weight, low-bulk profile. Instead, many of the patented designs require a multiplicity of securing straps and layers of foam rubber, thereby resulting in increased bulk and weight. Moreover, the so-called customized fit is achieved by wrapping one or more layers of foam rubber, having generic dimensions, around the unique configuration of an individual's upper and lower leg, and securing the foam wrapping by the use of numerous adjustable securing straps.

Reference is made to U.S. Pat. Nos. 4,852,557, 41928, 678, and 4,996,979, which provide formable orthopaedic cast or splint systems adapted to the unique configuration of an injured or broken limb. These splint systems, however, are directed exclusively to immobilizing a single straight limb, such as the lower arm or lower leg. Further, these designs may require supplemental support splints or ribs to provide the requisite degree of rigidity. In addition, these references disclose formable members which are adapted to surfaces requiring minimal curvature; the desired custom fit resulting from a wrappable foam sleeve and an inter-meshing hook and loop fastener material (commonly known as "VELCRO") strap system, rather than from the formable member.

Further reference is made to U.S. Pat. No. 5,042,464 to Skwor et al. which discloses the use of rigid cuffs and a formed resilient pad which is intended to accommodate the differences in configuration between the standard configuration rigid cuffs and the user's leg shape. The orthotic knee brace of Skwor et al. discloses a pad which includes a conformable, pliable, curable foam sheet. Not only is the pad initially pliable when placed around the user's leg, but the pad remains resilient even after it is cured. Accordingly, Skwor et al. teach the use of a resilient pad with a standard rigid curved cuff member, a structural combination which does not, in general actually match the shape of the user's leg, which does not provide optimal support, and which additionally requires cumbersome mechanical fasteners.

Accordingly, principal objectives of the present invention are to provide an orthopaedic custom "in situ" formable knee brace suitable for vigorous athletic activities which is lightweight, truly, uniquely and completely formable to the individual's leg and knee configuration, and easily fitted and removed. Additional objectives of the present invention are to provide a custom formable knee brace which is simpler to fabricate, may be custom formed "in situ" in a short time, is formed to the shape of the thigh and calf in its entirety and becomes substantially rigid in its conformation to the shape of the leg of the user, and is significantly less expensive than functional braces made in accordance with conventional methods, such as those described hereinabove. In accomplishing these objectives, the invention will increase the stability of the weakened or injured knee joint and insure the prevention of undesirable movements which could further injure the knee joint or complicate its healing.

SUMMARY OF THE INVENTION

Generally, the custom formable knee brace of the present invention is custom formed "in-situ" or in place with femoral and tibial soft-goods type components being pivotally connected, and with the components being formed of gas or liquid permeable material impregnated with an activatable, hardenable material which structurally conforms to the shape of the femoral and/or tibial surfaces when activated.

The components are preferably secured to the upper and lower leg by straps which may include "VELCRO"-type material or other fastening arrangements to hold them in place, during both activation of the hardenable material, and thereafter while the knee brace or support is in use.

In accordance with the specific illustrative embodiment of the present invention, a custom formable knee brace includes a femoral brace component sized to be circumferentially fitted over a femoral portion of a leg, a tibial-fibular brace component sized to be circumferentially fitted over a tibial-fibular portion of the leg, a liquid or gas permeable matrix fitted to the femoral brace component or to the tibial-fibular brace component, the matrix including a hardenable material which, when hardened, forms a substantially rigid structural member with the femoral brace component or the tibial-fibular brace component, the substantially rigid structural member being resistive to local deformities thereof from pressures applied to the substantially rigid structural member, and a hinge assembly pivotally connecting the femoral brace component to the tibial-fibular brace component.

In accordance with one aspect of the invention, the portions of the femoral and tibial-fibular components which extend in the circumferential direction around the upper or lower leg are free from any preformed rigid material which could inhibit full conformation to the configuration of the upper and lower leg.

In accordance with another aspect of the present invention, a knee brace is provided which includes an upper assembly extending generally longitudinally along the thigh, a lower assembly extending generally longitudinally along the tibia and calf, and hinge assemblies connecting the upper and lower assemblies which have their axes of rotation corresponding generally to the axis of rotation of the knee joint. The upper assembly includes a pair of elongated support struts extending along opposite sides of the thigh. The femoral component extends circumferentially around the anterior (frontal portion) femur, having opposed ends being fastened to the upper support struts. The upper assembly is secured to the wearer's thigh by use of a strap extending circumferentially around the posterior (back or hindermost) femur, with opposed ends being secured to the support struts.

Concerning another aspect of the invention, the lower assembly includes a pair of elongated support struts extending along opposite sides of the tibia and calf. The tibial component extends circumferentially around the anterior tibial crest (bony prominence on the lower leg just below the knee cap), having opposed ends being fastened to the lower support struts. The upper and lower support struts may be constructed from high-strength steel or other metals or alloys, engineering plastics, or other composite materials. An additional calf component may be provided, extending circumferentially around the wearer's calf, and having opposed ends affixed to the lower assembly's support struts.

In accordance with another aspect of the invention, condylar component pads may be included to provide support and comfort at the prominences on the inner and outer sides of the knee joint area. The condylar component pads may contain activatable, hardenable material which, when activated, harden and conform to the contour of the knee joint.

In accordance with another aspect of the present invention, each formable component may include a single or a multiplicity of formable pouches which encapsulate a water-activatable, hardenable urethane impregnated matrix, formed of material such as open cell foam, honeycomb material, fiberglass, "KEVLAR" carbonaceous fibers, or other similar materials. The pouch encloses the unpolymerized matrix, or other hardenable material, which begins the polymerization and hardening process upon the introduction of water or other activation chemistry.

In accordance with yet another aspect of the invention, a water and gas impermeable pouch may encompass the entire soft-goods type formable component assembly, the formable component having arrangements for introducing water to reach and activate the entire urethane impregnated material therein.

In accordance with additional aspects of the invention, the formable knee brace may be fastened to an individual's leg to stabilize an injured or weakened knee. The initially pliable femoral component is positioned about the anterior femur, being secured thereon by at least one strap extending circumferentially around the posterior femur, which may include "VELCRO"-type material or other fastening arrangements. The hinge assemblies are positioned on opposite sides of the knee joint. The initially pliable tibial component is positioned about the anterior tibial crest, and held in place by at least one strap extending circumferentially around the wearer's calf, which may be secured by means of "VELCRO"-type material or other fastening arrangements. Upon the secure tightening of the femoral and tibial components, and the introduction of water into the hardenable material, the urethane impregnated matrix polymerizes, hardens, and conforms to the unique shape of the wearer's femoral and tibial surfaces respectively.

In accordance with another feature of the invention, only the tibial component of the knee brace may be formed of liquid-permeable material impregnated with an activatable, hardenable material, while the femoral component may be a semi-circular collar structure, with both components being secured to the leg by straps.

In accordance with another aspect of the invention, the formable component may be detachable from its supporting assembly. The formable component may initially be enclosed within waterproof storage packaging, the water-activatable, hardenable material being enclosed in a water-permeable pouch so that when the soft-goods type component is to be used, the outer waterproof packaging is opened, and water is applied to the hardenable material, thus activating the polymerization reaction. After applying sufficient water, the formable component may be applied to the appropriate leg surface, and secured to the leg by straps, allowing the component to harden and form to the unique configuration of the leg.

In accordance with yet another aspect of the invention, the water may be delivered into the component cavity by means of an inlet port which may include a one-way valve. Arrangements are provided for distributing the water from the inlet port into the component cavity to saturate and activate the entire matrix which is impregnated with the water-activatable, hardenable material. This may be accomplished through the use of a distribution manifold or plenum separated from the matrix by a perforated plastic sheet; the plastic sheet having a diminishing number of progressively smaller holes in areas nearest the inlet port, and a greater number of progressively larger holes in areas furthest from the inlet port. After passing through the inlet port, the water may flow over, and through, the perforated distribution manifold, thereby contacting the impregnated substrate or matrix and initiating polymerization. This arrangement insures that the water flows into, and contacts the matrix in a uniform manner. An outlet vent may be provided to permit the escape of air and gases evolving from the polymerization reaction.

Alternatively, there could be a water delivery system wherein the inlet port is coupled to tubes incorporated within the component which breakout in a tree fashion so that small tubes extend to all areas of the matrix to insure uniform contact with the introduced water. Larger formable components may include a plurality of inlet ports and distribution assemblies. Additionally, each matrix may be sized to define an internal reservoir sized to receive a predetermined volume of the activating liquid or gas therein.

In accordance with another aspect of the invention, the activatable, hardenable material may be encapsulated in an airtight and moisture-proof pouch constructed of multiple layers of materials, typically layers of plastic and metallic foil. These combinations would make the pouch structurally strong as well as gas and moisture impermeable, with the plastic providing the strength, and the foil being airtight. Certain known flexible plastic materials are also sufficiently airtight and moisture-proof, which could be used alone without the supplemental metallic foil.

In accordance with yet another aspect of the invention, the inner structure of the pouch in which the activatable, hardenable material is enclosed, may be provided with an inlet port through which water and/or other chemical substances are supplied, and an outlet vent for the escape of air or other gases as fluid is supplied through the inlet port.

In accordance with another aspect of the invention, the soft-goods type, formable orthopaedic brace may have special configurations applicable to any desired jointed portion of the anatomy, such as the elbow joint, as a specific example.

It is further noted that another feature of the invention may include an inner layer of tricot, brushed nylon, or other fabrics to engage the wearer's skin. An additional thermal protective layer may be included to protect against any heat of reaction during polymerization of the activatable, hardenable material.

One advantage of the present invention is the full conformation of the brace to the user's leg, without any ill-fitting standard rigid cuffs to hinder or hamper movement of the user.

Other objects, features, and advantages of the invention will become apparent from a consideration of the following detailed description and from the accompanying drawings.

BRIEF DESCRIPTION OF THE DRAWINGS

Other objects, features and advantages of the invention will become readily apparent upon reference to the following detailed description when considered in conjunction with the accompanying drawings, in which like referenced numerals designate like parts throughout the figures thereof, and wherein.

DETAILED DESCRIPTION OF THE PREFERRED EMBODIMENTS

Figures 1, 4, 5:
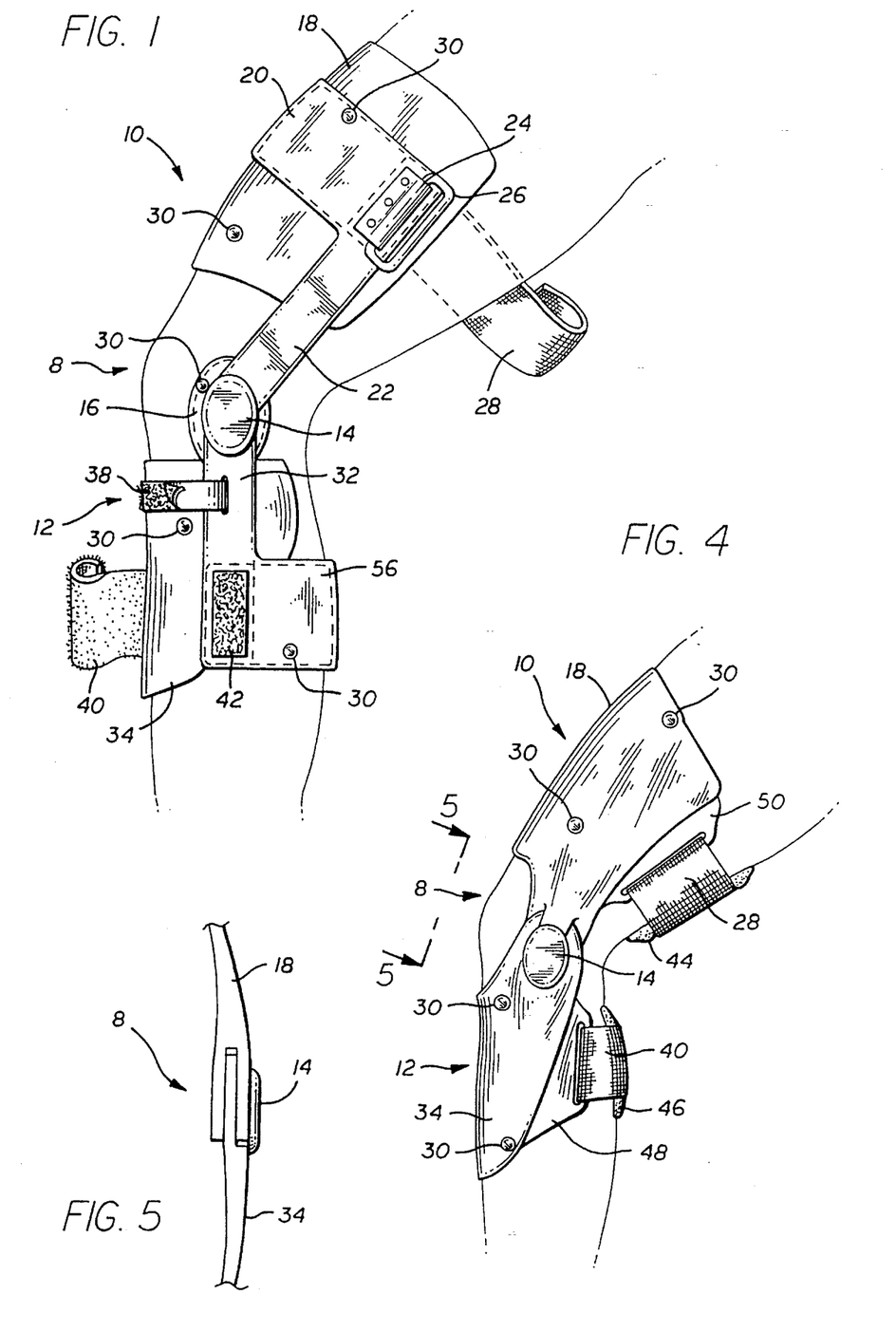
FIG. 1 is a view of a custom "in situ" formable knee brace illustrating the principles of the current invention in use on the wearer's leg.
FIG. 4 is a view of an embodiment of the invention used on the wearer's leg.
FIG. 5 is a frontal view through Plane VIII of FIG. 4 of a hinge assembly.

Referring more particularly to the drawings, FIG. 1 shows the formable knee brace 8 as it is used to stabilize the knee. FIG. 1 provides a view of knee brace 8 with an upper assembly 10, a lower assembly 12, and hinge assemblies 14 joining the upper and lower assemblies 10 and 12 respectively.

The upper assembly 10 includes femoral component 18 extending circumferentially around the wearers anterior femur. Femoral cuff 20 is shown mounted above femoral component 18, also extending circumferentially around the wearer's anterior femur. A pair of elongated support struts 22 extend along opposite sides of the femur so that the upper ends of support struts 22 are affixed to the opposed ends of femoral cuff 20 and femoral component 18 respectively. Buckle assembly 24 is mounted to the upper end of at least one of the support struts 22 and includes buckle loop 26. Strap 28, with one end attached to outer support strut 22 (not shown), extends circumferentially around the wearer's posterior femur, and is received by buckle loop 26.

As further illustrated in FIG. 1, inlet ports 30 are provided on the exterior surface of femoral component 18 and femoral cuff 20. A liquid or gas permeable material impregnated with an activatable, hardenable material is encapsulated within femoral component 18 and femoral cuff 20, both of which remain pliable and moldable until water is added to the permeable material. A predetermined volume of water may be injected into femoral component 18 and femoral cuff 20 via inlet ports 30. The water activates the urethane prepolymer matrix, which causes femoral component 18 and femoral cuff 20 to harden and conform to the unique shape of the wearer's anterior femur upon completion of the chemical reaction. Through the use of strap 28, upper assembly 10 is firmly secured to the wearer's thigh so that, upon the introduction of water, the activated polymer hardens into a substantially rigid structural member and takes a form or set uniquely conforming to the configuration of the wearer's thigh. In a preferred embodiment, strap 28 is of a "VELCRO"-covered type allowing for incremental adjustment of the constraining force of upper assembly 10 around the wearer's thigh.

Hinge assemblies 14 join together upper and lower assemblies 10 and 12. The lower ends of the support struts 22 are affixed to one side of hinge assemblies 14. A second pair of elongated support struts 32, are affixed to the other side of hinge assemblies 14. In accordance with one embodiment of the invention, hinge assemblies 14 are of a single-axis type with their axes of rotation coinciding with the axis of rotation of the knee joint. It should be noted that in a preferred embodiment, hinge assemblies 14 have an adjustable range of motion to allow the knee brace to simulate the natural bending of the knee or to limit the rotation of the knee joint.

Condyle pads 16 are mounted on the interior surface of hinge assemblies 14, providing support and comfort for the knee joint. In a preferred embodiment, condyle pads 16 encapsulate activatable, hardenable material therein, and include at least one inlet port 30. Condyle pads 16 may include a rubber or molded elastomer exterior. Water may be injected into condyle pad 16 through inlet port 30, thereby activating the urethane prepolymer therein, which causes condyle pad 16 to harden and conform to the unique shape of the knee joint upon completion of the chemical reaction.

Lower assembly 12 includes tibial component 34 extending circumferentially around the wearer's anterior tibia. Tibial component 34 may be permanently or, alternatively, detachably mounted to lower assembly 12, having at least one attachment site on each of the support struts 32. A detachable mounting assembly would preferably include a "VELCRO"-type attachment system to removably affix tibial component 34 to support struts 32.

The upper portion of tibial component 34 is held in place on the wearer's upper anterior tibia through the use of strap 38. Strap 38, with one end affixed to one of the support struts 32, extends circumferentially around and encompasses tibial component 34, and is adjustably secured to the opposite supporting strut 32. At least one inlet port 30 is provided on the exterior surface of tibial component 34, through which water may be injected to reach the activatable, hardenable material encapsulated therein. The water activates the urethane prepolymer, which causes tibial component 34 to harden and conform to the unique shape of the wearer's anterior tibia upon completion of the chemical reaction.

The lower portion of tibial component 34 is held in place against the wearer's anterior tibia through the use of strap 40. Strap 40, with one end secured to one of the support struts 32, extends circumferentially around and encompasses tibial component 34, and is adjustably secured to the opposite supporting strut 32.

In a preferred embodiment, straps 38 and 40 are of a "VELCRO"-covered type. The "VELCRO"-covered strap 40 is secured to supporting strut 32 by attachment to "VELCRO"-covered mating pad 42. It may be noted that in a preferred embodiment, support struts 22 and 32 are made of relatively lightweight, but stiff, material capable of resisting torsion and bending forces. High-strength steel, engineering plastics or composites are suitable materials for this application.

Calf component 56 extends circumferentially around the wearer's calf, having opposed ends affixed to the lower ends of support struts 32. At least one inlet port 30 is provided for introducing water into the activatable, hardenable material encapsulated within calf component 56. The water activates the urethane prepolymer which causes calf component 56 to harden and conform to the unique shape of the wearer's calf.

Figures 2, 3:
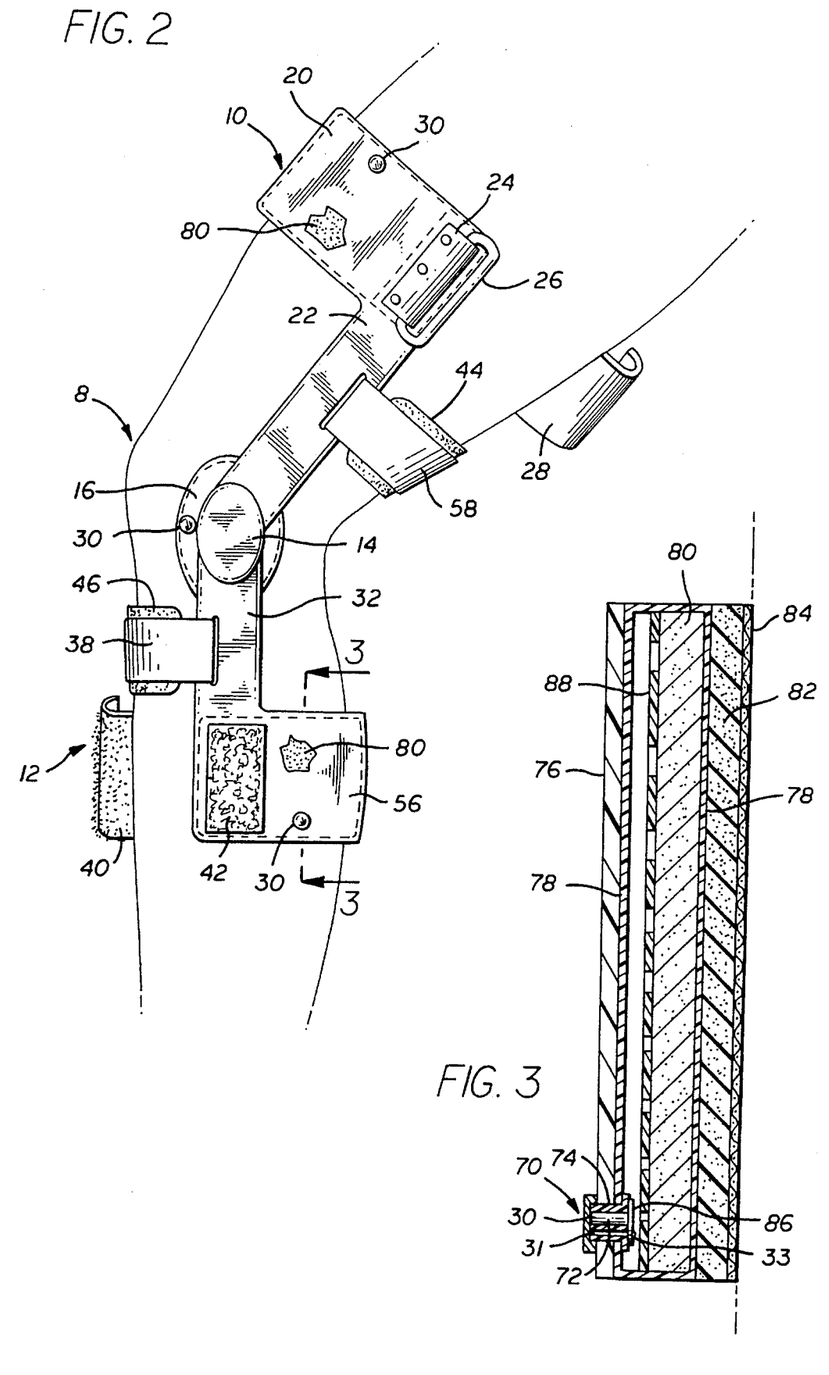
FIG. 2 illustrates an embodiment of the invention used on the wearer's leg.
FIG. 3 is a cross-sectional view through Plane III of FIG. 2, with a detailed showing of the component's structural configuration.

In accordance with one embodiment of the invention, as illustrated in FIG. 1, femoral component 18 may cover substantially more femoral surface area than that covered by femoral cuff 20. In another embodiment, as represented in FIG. 2, femoral component 18 may be excluded from upper assembly 10, with femoral cuff 20 being the primary femoral support member. Similarly, tibial component 34 may be replaced by a strap 38 and padding 46 assembly. This embodiment is particularly suitable for use by postoperative patients having surgical incisions around the knee area which cannot tolerate undue stress and pressure resulting from contact with the support surfaces of the knee brace 8. As also illustrated in FIG. 2, secondary strap 58, with opposed ends being attached to inner and outer support struts 22 respectively, extends circumferentially around the wearer's lower posterior femur. Cushioning pad 44 is affixed to secondary strap 58, providing increased comfort.

Lower assembly 12, as pictured in FIG. 2, is secured to the wearer's lower leg by straps 38 and 40, and calf component 56. Cushioning pad 46 is secured to strap 38. "VELCRO"-covered strap 40, having one end affixed to the lower end of outer support strut 32 (not shown), extends circumferentially around the anterior tibia, being adjustably secured to the lower end of inner support strut 32 via "VELCRO"-covered mating pad 42.

FIG. 3 shows a detailed cross-sectional view through Plane III of calf component 56 pictured in FIG. 2. It should be understood that the structure presented in FIG. 3 may be substantially similar to that included in femoral component 20, tibial component 34, and condyle component pad 16 pictured in FIG. 1. Each component contains a liquid or gas permeable substrate or matrix 80 impregnated with an activatable, hardenable urethane prepolymer. Substrate or matrix 80 can be comprised of open cell foam, fiberglass, or any other suitable carrier material for the urethane prepolymer. A honeycomb structure or a matrix of "KEVLAR" or graphite, or other high-strength fibers could also be employed, impregnated with activatable, hardenable material, and having an open configuration to receive the water for activation. The carrier materials may also consist of various fibers of different configurations such as knits and weaves. The knits provide a conforming material which easily and effectively drapes over bony prominences, such as the anterior tibial crest, while the woven materials provide directional strength in needed areas, such as hardware interfacing joints.

Composite layer 78, which may be formed of several alternating layers of foil and plastic, is airtight and impervious to water, and completely encapsulates matrix 80. Underneath composite layer 78 is a layer of foam 82. Contact liner 84 may include vinyl or brushed nylon, and may additionally include a thin layer of tricot, being soft to the touch, which engages the skin. Contact liner 84 will allow a certain amount of air to flow to the skin, and the tricot provides a soft interface between the component assembly and the skin. Between contact liner 84 and foam 82, an additional layer of insulating material (not shown) may be provided to further protect the skin from any heat of reaction that may occur from the polymerization reaction of the urethane prepolymer. Some of the larger embodiments, such as femoral component 18 indicated in FIG. 1, may generate sufficient heat which could cause discomfort to the wearer. In such cases, a protective insulating layer may be appropriate.

Flexible shell 76 may be formed of vinyl, pliable plastic, or other elastomer materials to provide a water-impervious outer shell directly covering composite layer 78. Inlet port 30 and outlet vent 31 are covered by removable cap 70 attached to port stem 74, with a water entry canal 72 contained therein. Optional one-way valving action may be provided by plastic port flaps 86 and 33 on inlet port 30 and outlet vent 31 respectively. A water injecting means, such as a syringe, may be coupled to water canal 72 through which a predetermined volume of water is injected, so that the water comes into contact with, and is distributed by, apertured manifold 88 which runs generally parallel to the surface of matrix 80. It is desirable that water introduced through inlet port 30 be uniformly applied to matrix 80 to activate and harden the entire urethane impregnation. To facilitate this action, apertured manifold 88, preferably fashioned from plastic, need only be a few thousands of an inch thick. Apertured manifold 88 may have fewer and smaller holes near inlet port 30, and an increasing number of larger holes at the component's remote ends. Outlet vent 31 permits the escape of air or other gases evolving from the polymerization reaction, which may be located adjacent inlet port 30.

In accordance with one embodiment of the invention, as illustrated in FIG. 4, femoral component 18 and tibial component 34 may constitute the primary support surfaces of upper assembly 10 and lower assembly 12 respectively. Femoral component 18 is shown covering a large area of the wearers anterior femur, and tibial component 34 is shown covering a large area of the anterior tibia. The process of forming the custom formable knee brace 8 to the wearer's unique upper and lower leg configuration begins by placing the initially pliable femoral component 18 on the wearer's front thigh adjacent the knee, and securing femoral component 18 thereon through the strap 28. Strap 28, with one end being fastened to flange 50 on one of the opposed ends of femoral component 18 (not shown), extends circumferentially around the wearer's posterior femur, passing through the strap slit in flange 50 affixed to the other opposed end of femoral component 18, and is secured to strap 28 thereon, preferably by means of "VELCRO" material affixed to strap 28. In a similar manner, the initially pliable tibial component 34 is placed on the wearer's anterior tibia adjacent the knee, and secured through the use of strap 40. Strap 40, with one end being fastened to flange 48 on one of the opposed ends of tibial component 34 (not shown), extends circumferentially around the wearer's calf, passing through the strap slit on flange 48, and is secured to strap 40 thereon, preferably by means of "VELCRO" material affixed to strap 40. Cushioning pads 44 and 46 are provided for comfort.

A predetermined volume of water is injected into femoral component 18 and tibial component 34 by means of inlet ports 30. The water polymerizes the urethane prepolymer matrix causing femoral component 18 and tibial component 34 to harden and conform to the unique and irregular shape of the wearer's anterior femur and anterior tibia respectively. The now-hardened custom formed femoral component 18 and tibial component 34 provide sufficient structural support to regulate the injured knee and prevent the pistoning effect, or downward shifting of the knee brace, resulting from walking or running. This embodiment of the invention provides the requisite structural support for the injured or weakened knee, provides a custom formed "in situ" fit unique to the individuals leg configuration, and exhibits a low-weight, low-bulk profile.

Upper assembly 10 and lower assembly 12 are joined together at hinge assemblies 14. It may be noted that in a preferred embodiment, hinge assemblies 14 are made of, or reinforced using, relatively lightweight, but stiff, material, such as high-strength engineering plastic. It may be further noted that the opposed lower ends of femoral component 18 and upper opposed ends of tibial component 34 integrally overlap to form hinge assemblies 14, as pictured in FIG. 5. Formable condylar pads may be included on hinge assemblies 14, and molded to the unique configuration of the knee joint. An additional layer of padding may be included on hinge assemblies 14 to provide additional comfort. Further, additional component thickness around hinge assemblies 14 may be included to provide additional structural support around the knee joint area, as shown in FIG. 5.

In accordance with another embodiment of the present invention, the areas around hinge assemblies 14 may include reinforcing support surfaces or members fashioned from high-strength steel or engineering plastic integrally contained within femoral and tibial components 18 and 34, and hidden from view. Strap flanges 50 and 48 may be fashioned from similar engineering plastic or high-strength steel.

Figure 6:
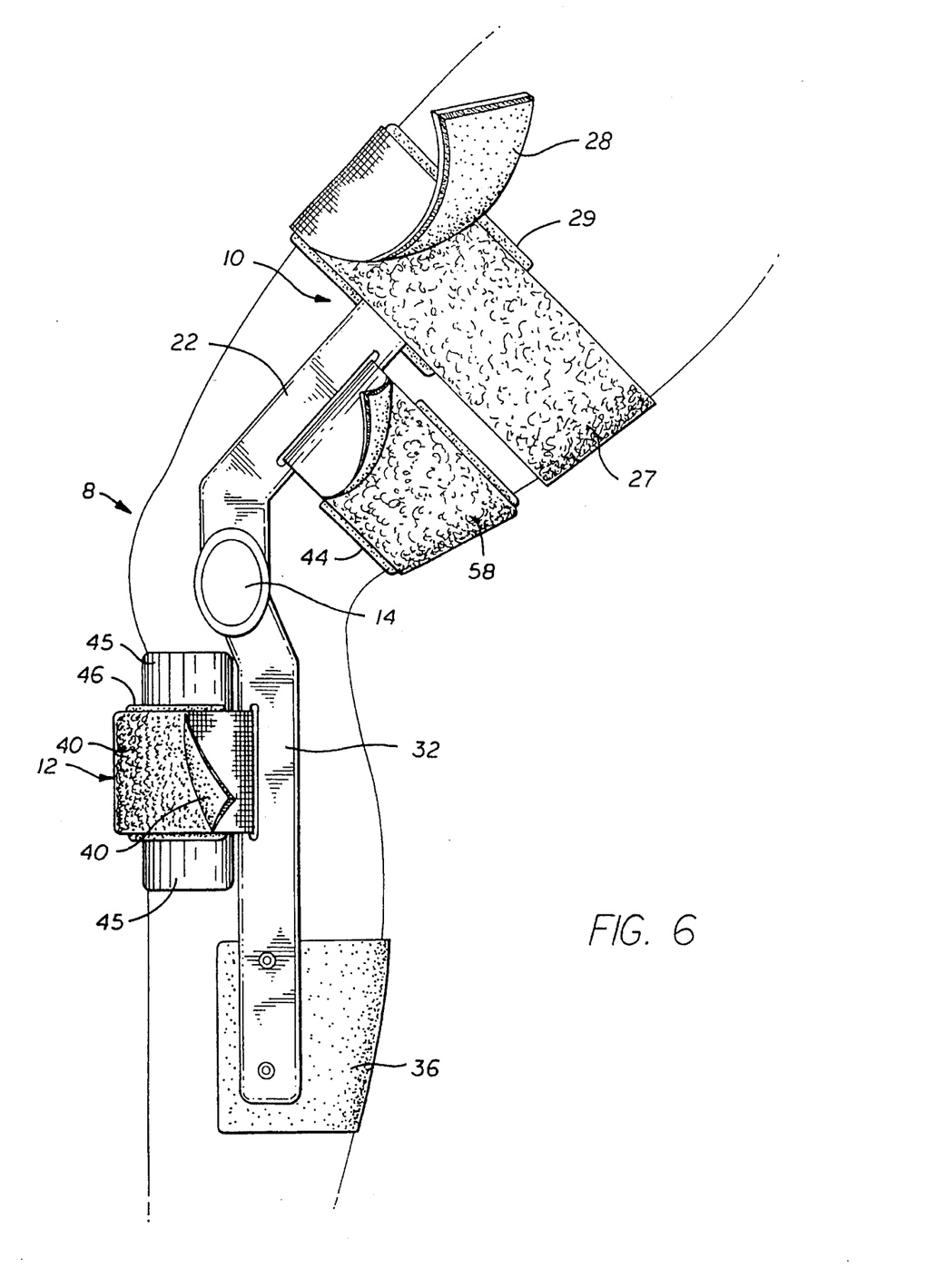
FIG. 6 illustrates a further embodiment of the invention used on the wearer's leg.

Turning now to FIG. 6, this figure provides a view of an alternative embodiment of the present invention incorporating a formable component into knee brace assembly 8. Upper assembly 10 includes a pair of support struts 22, femoral semi-circular steel collar 29 encased in foam, strap 58 extending circumferentially around the wearer's posterior femur including attached foam pad 44, and "VELCRO"-covered collar 27 extending circumferentially and encircling the wearer's thigh, encompassing femoral collar 29, and being adjustably secured through the use of "VELCRO"-covered tongue 28 and the mating "VELCRO" material on collar 27. Upper assembly 10 and lower assembly 12 are joined at hinge assemblies 14. Lower assembly 12 includes foam calf cuff 36 affixed to the lower ends of support struts 32, extending circumferentially around the wearer's calf.

Tibial component 45 extends around the wearer's anterior tibial crest and is held firmly against the anterior tibia through the use of "VELCRO"-covered strap 40. Strap 40, having one opposed end being attached to outer support strut 32 (not shown), the other end passing through the strap slit on inner support strut 32, is adjustably fastened onto itself via "VELCRO" receiving and attachment material on strap 40. Cushioning pad 46 is shown located between strap 40 and tibial component 45.

In one embodiment of the invention, as illustrated in FIG. 6, tibial component 45 may be detachable from the foam 46 and strap 40 assembly using a "VELCRO"-type attachment system. The initially pliable tibial component 45 may be of a construction similar to that pictured in FIG. 3. Alternatively, tibial component 45 may be of a different construction, one in which water is introduced into the impregnated matrix through a semi-permeable, porous covering. Such a construction need only be immersed in water to activate the prepolymer urethane once activated, the tibial component 45 is placed around the wearer's anterior tibial crest adjacent the knee. The detachable tibial component 45 is reattached to the foam 46 and strap 40 assembly and firmly secured to the tibia using strap 40. Upon completion of the chemical reaction, typically between 3 to 5 minutes, the hardened tibial component 45 conforms to the unique and irregular configuration of the wearer's anterior tibia. The entire semi-permeable porous component, encasing the activatable, hardenable matrix, may be enclosed within a gas and liquid impervious storage pouch to prevent premature activation.

In some cases, the outer surface of formable component 45, the fit of component 45 over the tibial crest area and the inner surface of the foam member 46, may be such that mating "VELCRO"-type material may not be needed to secure the tibial component 45 to the foam member 46.

It is to be understood that the foregoing description of the accompanying drawings shall relate to preferred and illustrated embodiments of the invention. Other embodiments may be utilized without departing from the spirit and scope of the invention. Thus, by way of example and not of limitation, the number of upper and lower assembly straps may be varied from one per assembly, to 2 or more per assembly. Also, hinge assemblies 14 could include polycentric, rather than single-axis, hinges. Further, various parts of the invention could be fabricated from materials other than those discussed herein. Also, the adjustable securing straps may be of a design employing a conventional buckle assembly or a contemporary design employing "VELCRO"-type materials. Further, upper and lower assembly struts 22 and 32 respectively can be fashioned from high-strength steel or engineering plastic, or other similar high-strength materials and composites. Moreover, femoral component 18, tibial component 34, calf component 56, and condylar component pad 16 may be of a single open cell design or may include a multiplicity of open cells of a construction similar to that pictured in FIG. 3. Alternatively, the activatable, hardenable material may be contained within a semi-permeable or porous capsule or multiplicity of capsules contained within each component assembly, which can be activated by simply immersing the component assembly in water. Furthermore, the activatable, hardenable material may include a two-part isocyanate prepolymer composition, or may be composed of other known materials as disclosed in U.S. Pat. No. 4,996,979 and the references cited therein.

Accordingly, it is to be understood that the detailed description and drawings set forth hereinabove are for illustrative purposes only and do not constitute a limitation on the scope of the invention.

What is claimed is:

1. A custom formable knee brace comprising:

a femoral brace component sized for circumferential fitting over an anterior femoral portion of a leg, said femoral brace component including a first liquid or gas permeable matrix impregnated with a first hardenable material, said first matrix forming a substantially rigid structural member of said femoral brace component when said first hardenable material is hardened, the portions of said substantially rigid structural member of said femoral brace component extending in a circumferential direction around the femoral portion of the leg being free of any preformed rigid material which could inhibit full conformation of said substantially rigid structural member of said femoral brace component to a configuration of the femoral portion of the leg, said substantially rigid structural member of said femoral brace component being resistive to local deformities thereof from pressures applied to said femoral brace component;

a first liquid or gas impervious composite layer within which said first matrix is enclosed;

a first apertured manifold enclosed within said first composite layer and positioned generally parallel to said first matrix, said first composite layer and said first apertured manifold defining a first reservoir sized to receive a predetermined volume of a first liquid or gas therein;

a first canal structure defining a first inlet port in said first composite layer facilitating an injection of the first liquid or gas into said first reservoir bringing the first liquid or gas into contact with said first apertured manifold for evenly distributing the first liquid or gas throughout said first matrix;

a tibial brace component sized for circumferential fitting over an anterior tibial portion of the leg, said tibial brace component including a second liquid or gas permeable matrix impregnated with a second hardenable material, said second matrix forming a substantially rigid structural member of said tibial brace component when said second hardenable material is hardened, portions of said substantially rigid structural member of said tibial brace component extending in a circumferential direction around the tibial portion of the leg being free of any preformed rigid material which could inhibit full conformation of said substantially rigid structural member of said tibial brace component to a configuration of the tibial portion of the leg, said substantially rigid structural member of said tibial brace component being resistive to local deformities thereof from pressures applied to said tibial brace component;

a second liquid or gas impervious composite layer within which said second matrix is enclosed;

a second apertured manifold enclosed within said second composite layer and positioned generally parallel to said second matrix, said second composite layer and said second apertured manifold defining a second reservoir sized to receive a predetermined volume of a second liquid or gas therein;

a second canal structure defining a second inlet port in said second composite layer facilitating an injection of the second liquid or gas into said second reservoir bringing the second liquid or gas into contact with said second apertured manifold for evenly distributing the second liquid or gas throughout said second matrix; and hinge assemblies pivotally connecting said femoral brace component to said tibial brace component.

2. The custom formable knee brace of claim 1 wherein said first hardenable material and said second hardenable material each comprise a material which hardens when exposed to a liquid or gas.

3. The custom formable knee brace of claim 2 wherein said first reservoir is sized to receive a predetermined volume of a first liquid or gas sufficiently great to harden substantially all of said first hardenable material and said second reservoir is sized to receive a predetermined volume of a second liquid or gas sufficiently great to harden substantially all of said second hardenable material.

4. The custom formable knee brace of claim 1 wherein said first hardenable material and said second hardenable material each comprise an urethane pre-polymer.

5. The custom formable knee brace of claim 1 wherein said first composite layer and said second composite layer each comprise a plurality of alternating layers of foil and plastic.

6. The custom formable knee brace of claim 1 wherein said hinge assemblies comprise condyle pads.

7. A custom formable knee brace comprising:

a femoral brace component sized for circumferential fitting over an anterior femoral portion of a leg, said femoral brace component including a first liquid or gas permeable matrix impregnated with a first hardenable material, said first matrix forming a substantially rigid structural member of said femoral brace component when said first hardenable material is hardened, the portions of said substantially rigid structural member of said femoral brace component extending in a circumferential direction around the femoral portion of the leg being free of any preformed rigid material which could inhibit full conformation of said substantially rigid structural member of said femoral brace component to a configuration of the femoral portion of the leg, said substantially rigid structural member of said femoral brace component being resistive to local deformities thereof from pressures applied to said femoral brace component;

a tibial brace component sized for circumferential fitting over an anterior tibial portion of the leg, said tibial brace component including a second liquid or gas permeable matrix impregnated with a second hardenable material, said second matrix forming a substantially rigid structural member of said tibial brace component when said second hardenable material is hardened, portions of said substantially rigid structural member of said tibial brace component extending in a circumferential direction around the tibial portion of the leg being free of any preformed rigid material which could inhibit full conformation of said substantially rigid structural member of said tibial brace component to a configuration of the tibial portion of the leg, said substantially rigid structural member of said tibial brace component being resistive to local deformities thereof from pressures applied to said tibial brace component; and a hinge assembly pivotally connecting said femoral brace component to said tibial brace component.

8. The custom formable knee brace of claim 7 further comprising:

a first liquid or gas impervious composite layer within which said first matrix is enclosed; and a second liquid or gas impervious composite layer within which said second matrix is enclosed.

9. The custom formable knee brace of claim 8 further comprising:

a first apertured manifold enclosed within said first composite layer and positioned generally parallel to said first matrix;

a first canal structure defining a first inlet port in said first composite layer facilitating an injection of a first liquid or gas over said first apertured manifold for evenly distributing the first liquid or gas throughout said first matrix;

a second apertured manifold enclosed within said second composite layer and positioned generally parallel to said second matrix; and a second canal structure defining a second inlet port in said second composite layer facilitating an injection of a second liquid or gas over said second apertured manifold for evenly distributing the second liquid or gas throughout said second matrix.

10. The custom formable knee brace of claim 7 wherein said first hardenable material and said second hardenable material each comprise a material which hardens when exposed to a liquid or gas.

11. The custom formable knee brace of claim 7 wherein said first hardenable material and said second hardenable material each comprise a urethane pre-polymer.

12. The custom formable knee brace of claim 7 wherein said hinge assembly comprises a condyle pad.

13. A custom formable knee brace comprising:

a femoral brace component sized to be circumferentially fitted over a femoral portion of a leg;

a tibial-fibular brace component sized to be circumferentially fitted over a tibial-fibular portion of the leg;

a liquid or gas permeable matrix fitted to said femoral brace component or to said tibial-fibular brace component, said matrix including a hardenable material which, when hardened, forms a substantially rigid structural member with said femoral brace component or said tibial-fibular brace component, the portions of said substantially rigid structural member extending in a circumferential direction around the femoral portion or the tibial-fibular portion of the leg being free of any preformed rigid material which could inhibit full conformation of said substantially rigid structural member to a configuration of the femoral portion or the tibial-fibular portion of the leg, said substantially rigid structural member being resistive to local deformities thereof from pressures applied to said substantially rigid structural member; and a hinge assembly pivotally connecting said femoral brace component to said tibial-fibular brace component.

14. The custom formable knee brace of claim 13 wherein said liquid or gas permeable matrix is fitted to a surface of said femoral brace component facing an anterior femoral portion of the leg.

15. The custom formable knee brace of claim 13 wherein said liquid or gas permeable matrix is fitted to a surface of said tibial-fibular brace component facing an anterior tibial portion of the leg.

16. The custom formable knee brace of claim 13 wherein said liquid or gas permeable matrix is fitted to a surface of said tibial-fibular brace component facing a calf portion of the leg.

17. The custom formable knee brace of claim 13 further comprising:

a liquid or gas impervious composite layer within which said matrix is enclosed.

18. The custom formable knee brace of claim 17 further comprising:

an apertured manifold enclosed within said composite layer and positioned generally parallel to said matrix; and a canal structure defining an inlet port in said composite layer facilitating an injection of a liquid or gas over said apertured manifold for evenly distributing the liquid or gas throughout said matrix.

19. The custom formable knee brace of claim 13 wherein said hardenable material comprises a material which hardens when exposed to a liquid or gas.

20. The custom formable knee brace of claim 13 wherein said hardenable material comprises an urethane prepolymer.

* * * * *